(12) United States Patent
Margolis et al.

(10) Patent No.: US 6,340,591 B1
(45) Date of Patent: Jan. 22, 2002

(54) INTEGRATIVE PROTEIN-DNA COCHLEATE FORMULATIONS AND METHODS FOR TRANSFORMING CELLS

(75) Inventors: David Margolis, Baltimore, MD (US); Susan Gould-Fogerite; Raphael James Mannino, both of Annandale, NJ (US)

(73) Assignees: University of Maryland, Baltimore, MD (US); University of Medicine and Dentistry of New Jersey, Newark, NJ (US)

(*) Notice: Subject to any disclaimer, the term of this patent is extended or adjusted under 35 U.S.C. 154(b) by 0 days.

(21) Appl. No.: 09/210,578

(22) Filed: Dec. 14, 1998

(51) Int. Cl.[7] .................. C12N 15/63; A61K 48/00; C07H 21/04; C07K 14/00
(52) U.S. Cl. .................. 435/320.1; 435/458; 435/440; 424/450; 514/44; 530/350; 536/23.4; 536/23.5
(58) Field of Search ................ 424/450; 514/44; 435/320.1, 458, 440; 530/350; 536/23.5, 23.4

(56) References Cited

U.S. PATENT DOCUMENTS

| | | | |
|---|---|---|---|
| 5,827,703 A | * 10/1998 | Debs et al. ............... | 435/172.3 |
| 5,843,742 A | 12/1998 | Natsoulis et al. | |
| 5,972,899 A | * 10/1999 | Zychlinsky et al. ......... | 514/44 |
| 5,994,318 A | * 11/1999 | Gould-Fogerite et al. ..... | 514/44 |

FOREIGN PATENT DOCUMENTS

| | | |
|---|---|---|
| WO | WO96 15777 | 5/1996 |
| WO | WO96 25942 | 8/1996 |
| WO | WO97 30725 | 8/1997 |

OTHER PUBLICATIONS

Verma, I.M. et al. Gene therapy–promises, problems and prospects, Nature, vol. 389, 1997, pp. 239–242.*
Orkin, S.H. Report and Recommendations of the Panel to asssess the NIH investment in research on gene therapy, Dec. 1995.*
Eck, S.L. et al., 1996, Ch. 5. Gene Based Therapy,Goodman & Gillman's The Pharmacological basis of Therapeutics. p. 77–101.*
Lipofection Of Purified Adeno–Associated Virus Rep68 Protein: Toward A Chromosome–Targeting Nonviral Particle, Stefania LaMartina, Guiseppe Roscilli, Daniela Rinaudo, Paola DelMastro and Carlo Toniatti, Journal Of Virology, vol. 72, No. 9, p. 7653–7658, Sep. 1998.
Shoji–Tanaka et al, Biochem. and Biophys. Res. Comm., 203:1756–1764 (1994).
Gould–Fogerite et al, Adv. Drug. Delivery Rev., 32:273–287 (1998).

* cited by examiner

Primary Examiner—Scott D. Priebe
Assistant Examiner—Eleanor Sorbello
(74) Attorney, Agent, or Firm—Sughrue Mion, PLLC (57) ABSTRACT

An integrative DNA vector and one or more viral proteins having affinity for DNA are packaged in cochleate precipitates. The integrative DNA vector contains one or more therapeutic nucleotide sequences that are preferably positioned between DNA substrates for the proteins. Upon contact with a lipid bilayer of a target cell, the cochleate vector structure delivers one or more of the therapeutic nucleotide sequences and one or more proteins to the interior of the target cell. Upon entry into the cell, the proteins facilitate the integration of the therapeutic nucleotide sequence into the genome of the host cell.

28 Claims, 3 Drawing Sheets

FIG. 3B

INTEGRATIVE PROTEIN-DNA COCHLEATE FORMULATIONS AND METHODS FOR TRANSFORMING CELLS

BRIEF DESCRIPTION OF THE INVENTION

The present invention relates to a lipidic vector system comprising a multi-layered lipid bilayer structure called a cochleate precipitate. The layers of the lipid bilayer structure are ionically bound together by a cation.

One or more therapeutic nucleotide sequences coding for a therapeutically beneficial molecule and one or more proteins that facilitate integration of the therapeutic nucleotide sequences physically associated with the cochleate precipitate.

The proteins are preferably adeno-associated virus (AAV) Rep 68 and Rep 78. The therapeutic nucleotide sequence is preferably positioned between AAV inverted terminal repeats (ITRs).

Upon contact with a lipid bilayer of a target cell, the cochleate vector structure delivers one or more of the therapeutic nucleotide sequences and one or more of the proteins to the interior of the target cell. Upon entry into the cell the one or more proteins facilitate the integration of the therapeutic nucleotide sequence(s) into the genome of the host cell.

BACKGROUND OF THE INVENTION

Recent advances in molecular biology have increased the scientific understanding of the genetic basis for disease and have provided the tools for novel advances in gene therapy. For example, it is now possible to produce genetically engineered nucleotide sequences capable of expressing therapeutic molecules. Yet, major obstacles have remained, and one such obstacle has been the lack of effective means for delivering these therapeutic nucleotide sequences to the interior of a target cell in a form capable of integrating into the target cell's genome. This invention relates to a vector delivery system capable of delivering genetic materials to the interior of a cell along with the molecules necessary for the integration of such genetic materials into the genome of the target cell.

The vector delivery system of the present invention comprises a lipidic structure called a cochleate precipitate or, simply, a cochleate. The cochleate comprises a multi-layered lipid bilayer structure. The multi-layered lipid bilayer structure generally comprises a membrane phospholipid containing a negatively charged head group and a cation such as calcium ($Ca^{++}$). The cation serves as a bridge, ionically binding to the negatively-charged head groups of the phospholipid groups and thus linking together the individual lipid bilayers of the limit-layered structure.

Cochleates consist of alternating sheets of cation-complexed lipid. In a preferred mode of the invention, the multi-layered lipid bilayer structure exists as a continuous lipid bilayer sheet rolled up into a spiral conformation. The cation maintains the cochleate structure by ionically binding to the negatively charged head groups in the opposing lipid bilayers. For example, where the cation is $C^{++}$, one positive charge of the $Ca^{++}$ attracts a negatively charged phospholipid headgroup in one bilayer, and the other positive charge attracts a phospholipid headgroup in the opposing bilayer.

Cochleates are highly stable and can be stored in calcium-containing buffer. Cochleates can also be lyophilized to a powder, stored at room temperature, and reconstituted with liquid prior to administration.

While other lipidic vector delivery systems are known (See Lee et. al., "Lipidic Vector Systems for Gene Transfer", Critical Reviews in Drug, Carrier Systems 14(2): 173–206 (1997)), they are typically in the form of liposomes and are substantially different from the cochleate vector delivery system described herein. A liposome is a fluid-filled compartment bounded by a fluid lipid bilayer. Materials, such as DNA or protein, can be contained within a liposome, and such materials can be delivered to the interior of a cell by endocytic uptake or, in special instances, fusion of the liposome with the cell membrane.

Unlike cochleate structures, harsh environmental conditions, such as extreme pH levels or the presence of lipid degrading enzymes, render the lipid bilayer of a liposome susceptible to instability and compromise the membrane barrier. Compromise of the membrane barrier renders the contents of the liposome subject to attack by external elements. For example, degradative enzymes, such as proteases and nucleases can degrade proteins and polypeptides within the compromised liposome.

An additional difference between liposomes and cochleate is the presence of divalent cations. Cochleates are prepared by calcium induced fusion of liposomes. Cochleates can contain, for example, one-half the molar concentration of divalent cations relative to the molar concentration of phospholipids. The divalent cations organize the negatively charged lipid bilayers into solid sheets that roll or stack upon themselves, excluding water.

Cochleates are multi-layered, highly stable structures composed of non-toxic and non-inflammatory natural products. They are solid, lyophilizable precipitates containing little or no internal aqueous space. Whereas dehydration of liposomes, e.g., by lyophilization, destroys the morphology and integrity of liposomes, such dehydration has no adverse effects on cochleate morphology or functions. The layers of the cochleate are composed of alternating sheets of negatively charged phospholipid and calcium. This unique structure protects associated, "encochleated," molecules from degradation. Since the entire cochleate structure is a series of solid layers, components within the interior of the cochleate structure remain intact even though the outer layers of the cochleate may be exposed to harsh environmental conditions or enzymes.

The formulation of integrative DNA protein complexes or the use of these complexes as gene transfer vehicles has not heretofore been described.

Calcium induced perturbations of membranes containing negatively charged lipids, and the subsequent, resulting membrane fusion events, are important mechanisms in many natural membrane fusion processes. Accordingly, while the definitive mechanism of cochleate delivery is unknown, it is hypothesized that cochleates act as membrane fusion intermediates. According to this theory, as the calcium rich membrane of a cochleate approaches a natural membrane, a perturbation and reordering of the cell membrane is induced, resulting in a fusion event between the outer layer of the cochleate and the cell membrane. This fusion results in the delivery of a small amount of the encochleated material into the cytoplasm of the cell. Theoretically, the cochleate can then break free of the cell and be available for another fusion event, either with this or another cell. Alternatively, the cochleate may be taken up by endocytosis, and fuse with the cellular membranes from within. In contrast, the lipid bilayer of most liposomes is highly thermodynamically stable and resists fusion with other liposomes or with other membrane bound structures.

The membrane fusion hypothesis is consistent with the observation that many naturally occurring membrane fusion events involve the interaction of calcium with negatively charged phospholipids, (generally phosphatidylserine and phosphatidylglycerol). This hypothesis is also consistent with experimental studies. For example, the ability of cochleates to mediate the induction of antigen specific, CD8+ cytotoxic lymphocytes supports the hypothesis that cochleates facilitate the cytoplasmic delivery of cochleate-associated macromolecules. And, immunological studies indicating a slow, long-term presentation of antigen are consistent with the theory that a single cochleate undergoes multiple fusion events over an extended period of time.

The present invention makes use of cochleates as delivery vehicles for genetic materials and proteins that facilitate integration of the genetic materials into the host genome. In one example, the genetic materials and proteins are from the adeno-associated virus (AAV). AAV is a naturally defective, single stranded DNA parvovirus that is commonly used as a vector.

Wild-type AAV generally requires co-infection with a helper virus in order to replicate. Without a helper virus, AAV integrates into the genome of the host cell and remains latent for extended periods of time. AAV has not been associated with any human disease, and the integration of AAV does not appear to affect cell replication. The propensity of the AAV genome to safely integrate into the genome of host cells makes it an attractive vector for gene therapy.

AAV encapsidated in viral structural proteins has been used as a vector for gene delivery. The present invention differs significantly in that it makes use of unencapsidated AAV genetic elements complexed with selected viral proteins, and packaged in cochleates.

The AAV genome is 4.68 kb in length and contains two open reading frames and two 145 bp inverted terminal repeats (ITRs) (Chatterjee et al, Science 258: 1485–88 (1992). The two open reading frames, located between the ITRs, contain the rep and cap genes, which contain proteins involved in replication and encapsidation, respectively. The AAV rep gene is transcribed from two promoters, $p_5$ and $P_{19}$. Transcription from the $p_5$ promoter generates mRNA transcripts that encode the Rep 68 and 78 proteins. Rep 68 and 78 are known to mediate complex formation between AAV DNA and its integration site in human DNA (See Weitzman et al., "Adeno-associated virus (AAV) Rep proteins mediate complex formation between AAV DNA and its integration site in human DNA," Proc. Natl. Acad. Sci. USA 91:5808–5812 (1994)). These proteins bind specifically to the AAV terminal hairpin, formed by the terminal 125 bases, and possess helicase and site-specific endonuclease activities required for AAV replication. Id.

One approach to utilizing the integrative capacity of the AAV system is to co-transfect cells with a vector expressing the Rep proteins along with a vector containing a gene to be transfered flanked by the ITR's. The difficulty with this approach is the potential chronic production of Rep and Cap proteins. Rep is known to have effects on the expression of some cellular genes and could be toxic at high levels. In particular, chronic expression of the proteins in hematopoietic stem cells could significantly alter their genetic program. This could lead to changes in differentiation patterns and potentials. The rep and cap genes can be excised and replaced by a nucleotide sequence containing one or more genes expressing one or more therapeutically effective molecules. However, as already mentioned, Rep 68 and Rep 78 are required for integration of the AAV genome into the genome of the target cell. The present invention solves this difficulty by packaging in vitro synthesized Rep 68 and Rep 78 proteins, along with AAV genetic material lacking the rep and cap genes. In a preferred embodiment of the invention, a cochleate is used to deliver an AAV DNA strand having the rep and cap genes excised and having one or more therapeutic genes spliced between the ITRs, copackaged with recombinant AAV Rep 68 and Rep 78 proteins.

A difficulty with the standard use of the AAV capsid to deliver AAV genetic materials is that the capsid size limits the length of the therapeutic nucleotide sequence that can be spliced between the ITRs. Due to the small size of the AAV capsid, nucleotide sequences over 5 kb integrate poorly. Since the AAV ITRs comprise at least 290 bases, approximately 4.7 kb are left for the therapeutic nucleotide sequence of interest. This upper limit rules out the use of larger nucleotide sequences that may be attractive candidates for gene therapy, such as the gene coding for dystrophin, the absence or dysfunction of which leads to Duchennic and Becker muscular dystrophy. In contrast, while the upper limit is not known for the number of bases that can be spliced between the AAV ITRs for delivery by the inventive cochleate vector system, it is predicted that this number will be much greater than the number of bases that can be spliced between the AAV ITRs for delivery by the AAV capsid. The capacity to deliver larger therapeutic nucleotide sequences should greatly increase the number of genetic disorders for which the AAV ITRs can be used as a vector.

Another advantage of the use of the cochleate as a packaging system for an AAV based plasmid is the ability to deliver the AAV genetic materials without contamination by helper viruses. The standard method for constructing AAV vectors involves the co-infection of a host cell with (1) the AAV genome having the rep and cap genes replaced by the gene of interest; (2) a helper plasmid containing the AAV rep and cap genes without the AAV ITRs, typically containing adenovirus promoters; and (3) a helper adenovirus. The AAV rep and cap genes produce the Rep and Cap proteins but cannot be encapsidated by the AAV capsid. The foreign gene flanked by the AAV ITRs is encapsidated in the AAV capsid by the action of the Rep and Cap proteins. The result is a mixture of recombinant AAV and adenovirus. The recombinant AAV must then be purified by buoyant density centrifugation with a risk of contamination by residual adenovirus. In contrast, the vector delivery systems of the present invention may be constructed without the aid of the helper adenovirus, thus eliminating the risk of adenovirus contamination.

An important aspect of the present invention is the transduction of hematopoietic stem cells. Hematopoietic stem cells are the undifferentiated, pluripotent progenitor cells from which other specialized blood cells develop. The ability to provide long-term correction of many genetic disorders of the hematopoietic cells is required for the reconstitution of other cells in the hematopoietic system.

Unfortunately, transduction of hematopoietic cells using, conventional retro-viral vectors requires the stimulation of such cells by cytokines. Cytokine stimulation is thought to destroy the pluripotent nature of these stem cells. The present inventors have surprisingly and unexpectedly discovered a means for transforming hematopoietic stem cells in the absence of cytokine stimulation, that results in the transduction of hematopoietic cells. Because this transduction occurs in the absence of cytokine stimulation, the integration into the host genome of the AAV genetic elements can be effected without disturbing the pluripotent capacity of hematopoietic stem cells. The present invention is therefore a major advance in the field of gene therapy, and particularly in the field of gene therapy for blood disorders.

It was not previously known that cochleates containing rep proteins and DNA with ITRs could serve as a vector for efficient delivery to the nucleus of the proteins and the DNA in a form suitable for rep protein catalyzed integration of the DNA.

It was also unexpected that the rep protein-DNA-cochleate complexes would retain functional association with long-term stability. Formulations stored for more than one year at 4° C. exhibited no detectable loss in efficiency of gene transfer.

DETAILED DESCRIPTION OF THE INVENTION AND OF THE PREFERRED EMBODIMENTS OF THE INVENTION

The present invention relates to a lipidic vector system comprising a layered lipid bilayer structure known as a cochleate precipitate. The individual lipid elements of the lipid bilayer contain a negatively charged head group. The layers of the lipid bilayer structure are bound together by an associated cation which is ionically bonded to the negatively charged head group.

Associated with the cochleate precipitate are one or more proteins that can facilitate the integration of the nucleotides into the genome of the host cell. In the preferred embodiment, AAV proteins are utilized.

Also associated with the cochleate bilayer is an oligonucleotide or polynucleotide containing a therapeutic nucleotide sequence and nucleotide sequences recognized by proteins having a DNA binding function. In a preferred embodiment, these DNA sequences recognized by proteins are the AAV ITRs. Preferably, the therapeutic nucleotides are positioned between the nucleotide sequences recognized by proteins having a DNA binding function.

The therapeutic nucleotide sequence codes for one or more therapeutically beneficial molecules. A therapeutically beneficial molecule according to the present invention is a therapeutic amino acid chain of any length, including shorter amino acid sequences commonly referred to as peptides, as well as longer amino acid sequences, commonly referred to as polypeptides or proteins. Many such therapeutically beneficial molecules are well known to one of ordinary skill in the art. In addition or alternatively, the RNA molecule expressed from the DNA sequence may be the active element, for example, the RNA may have anti-sense, catalytic, or protein-binding activity.

Upon coming into contact with the lipid bilayer of a target cell, the layered lipid bilayer can deliver one or more of the therapeutic nucleotide sequences and one or more proteins to the interior of the target cell. Upon entering into the cell, the protein or proteins facilitate the transfer into the nucleus and/or integration of the therapeutic nucleotide sequence into the genome of the host cell.

The cochleate precipitate vector structures used in the instant invention can be prepared by known methods such as those described in U.S. Pat. No. 5,643,574; U.S. Pat. No. 4,633,161; U.S. Pat. No. 4,871,488; S. Gould-Fogerite et al., *Analytical Biochemistry, Vol.* 148, pages 15–25 (1985); S. Gould-Fogerite et al., *Advances in Membrane Biochemistry and Bioenergetics*, edited Kim, C. H., Tedeschi, T. Diwan, J. J., and Salerno, J. C., Plenum Press, New York, pages 569–586 (1988); S. Gould-Fogerite et al., *Gene*, Vol. 84, pages 429–438 (1989); *Liposome Technology*, 2nd Edition, Vol. I, Liposome Preparation and Related Techniques, Vol. II, Entrapment of Drugs and Other Materials, and Vol. III, Interactions of Liposomes with the Biological Milieu, all edited by Gregory Gregoriadis (CRC Press, Boca Raton, Ann Arbor, London, Tokyo), Chapter 4, pp 67–80, Chapter 10, pp 167–184, and Chapter 17, pp. 261–276 (1993); R. J. Mannino and S. Gould-Fogerite, Liposome Mediated Gene Transfer, *Biotechniques*, Vol. 6, No. 1 (1988), pp. 682–690; and Miller et al., "Vaccination of rhesus monkeys with synthetic peptide in a fusogenic proteoliposome elicits simian immunodeficinecy virus-specific CD8+ cytotoxic T lymphocytes," *J. Exp. Med.* vol. 176, pp.1739–1744 (1992).

One method for encochleation ("trapping") involves addition of calcium to a suspension of lipid and material to be encochleated. This method generally proceeds as follows:

1. Lipid (and material to be encochleated if it is soluble in organic solvent) is dried to a thin film in a vessel. Alternatively, lipid in powdered form is used.
2. Buffer is added, and the lipid is suspended by agitation.
3. Aqueous soluble material to be encochleated is added to the liposome suspension.
4. The addition of a calcium solution results in the formation of sheets of calcium-chelated phospholipid bilayers.
5. The sheets roll up or stack to form cochleates containing the material of interest.

An alternative method for encochleation involves the removal of detergent from a solution of lipid and material to be encochleated, followed by, or concurrent with, addition of calcium.

1. Material to be encochleated is added to a solution containing a detergent (e.g. (β-D octylglucopyranoside in a high-salt buffer).
2. This solution is added to the natural lipids, phosphatidylserine and cholesterol.
3. The detergent is removed by dialysis resulting in the formation of small lipid vesicles.
4. The addition of calcium as a solution or by dialysis results in the formation of sheets of calcium-chelated phospholipid bilayers.
5. The sheets roll up or stack to form cochleates containing the material of interest.

The individual lipid elements of the layered lipid bilayer of the cochleates precipitates can be any of the many known lipid structures having a negatively charged polar head group. Preferably the majority of the lipid elements of the lipid bilayer contain a negatively charged phospholipid headgroup. Upon contact with a lipid bilayer of a target cell, the layered lipid bilayer is capable of delivering one or more of the therapeutic nucleotide sequences and one or more AAV proteins to the interior of the target cell.

Cochleate precipitates take the form of many physical structures within the limits of the technology, but which are functionally and physically distinguishable from liposomes. Cochleates have a nonaqueous structure while not having an internal aqueous space. In their physical state, cochleates have been observed as multilayered spiral or nonspiral forms, cylinders, particulates up to several microns in diameter, as well as needle-like structures.

The layers of the lipid bilayer structure of the cochleates are bound together by an associated cation (e.g., $Ca^{++}$, $Mg^{++}$, etc.) ionically bonded to the negatively charged polar headgroup. Preferably the cation is a divalent cation (e.g., $Ca^{++}$, $Mg^{++}$) and preferably the divalent cation is $Ca^{++}$. Associated with the cochleate precipitate is an oligonucleotide or polynucleotide containing a therapeutic nucleotide sequence coding for a therapeutically beneficial molecule, such as an RNA or a peptide or polypeptide or an enzyme or other protein.

The oligonucleotide or polynucleotide is preferably a supercoiled plasmid (but may be relaxed circular or linear). The oligonucleotide or polynucleotide also contains the AAV ITRs. Preferably the therapeutic nucleotide sequence is located between the AAV ITRs.

The therapeutic nucleotide sequence may include one or more therapeutic genes. A therapeutic gene may, for example, replace or supplement defective genetic material. For example, the therapeutic gene may replace genetic material that has been damaged by mutation events. A therapeutic gene could also code for RNA or protein which could interfere with the production, stability, or activity of an endogenous or foreign gene or gene product.

Alternatively, a therapeutic gene may add new genetic material to create a desirable new phenotype. For example, the therapeutic gene may code for a non-mammalian enzyme that converts a prodrug from an inactive to an active form. It is readily apparent to one of ordinary skill in the art that the number of possible therapeutic genes that can be employed with the present invention is immense and will naturally increase with the advance of knowledge of disease processes.

It will be appreciated that the therapeutic nucleotide sequence can include appropriate transcriptional and/or translational control elements. For example, the therapeutic nucleotide sequence may contain various transcriptional control elements, such as one or more promoters, upstream promoter elements, regulatory elements and/or enhancer elements. Tissue-specific and/or inducible expression of a therapeutic (gene may be achieved by the incorporation into the therapeutic nucleotide sequence of appropriate promoter/enhancer sequences.

The therapeutic nucleotide sequence may include one or more nucleotide sequences coding for various regulatory molecules, such as transcription factors. Such regulatory molecules may, for example, include various trans-acting elements.

The therapeutic nucleotide sequence may also include various marker elements to identify cells in which the therapeutic nucleotide sequence has successfully integrated into the host cell's genome.

The nucleotide sequences recognized by proteins having a DNA binding function include, but are not limited to sequences serving as substrates for integrase, helicase, excision enzymes, isomerase, telomerase, repair enzymes, or gene regulatory sequences.

The one or more proteins that bind to the nucleotide sequences or the target cell's genome and facilitate the integration of the therapeutic nucleotide sequence into such genome are packaged within the lipid bilayer along with the therapeutic nucleotide sequence. Upon entering the cell, the protein(s) are capable of facilitating the integration of the therapeutic nucleotide sequence into the genome of the host cell.

The proteins may, for example, be Rep proteins from the adeno-associated virus. In a preferred mode of the invention, the Rep proteins are selected from the group consisting of a Rep 68 protein of the adeno-associated virus and a Rep 78 protein of the adeno-associated virus. The invention preferably includes both Rep 68 and Rep 78 proteins of the adeno-associated virus.

Alternatively, other proteins that bind to DNA could be used. Such proteins include, but are not limited to, integrase, helicase, isomerase, telomerase, excision enzymes, or repair enzymes. Proteins facilitating transport to or uptake by the nucleus or proteins that have gene regulatory activities can also be used. Examples include proteins with nuclear transport signals include but not limited to SV40 T antigen, polyoma T antigen, normal proteins involved in DNA or RNA replication or gene regulation, or response to extracellular or intracellular signalling, such as NFκB, cyclins, protein kinases, hormone receptors, etc.

It will be appreciated that the target cell can be any cell to which the layered lipid bilayer is capable of delivering its contents. Methods for determining whether a cell is susceptible to transfection by a particular vector are well known to those of ordinary skill in the art of gene therapy and involve no more than routine experimentation. The target cell is preferably a human cell but may be a cell of any other primate or animal that is susceptible to transfection and integration by the cochleate vector structure in the presence of suitable proteins having a DNA binding function. Alternatively, the present invention may be applied to the delivery of DNA protein complexes to microorganisms or plants.

The invention may be delivered in vivo by any means which brings the layered lipid bilayer in contact with a target cell. Exemplary means of administration include oral, parenteral, rectal, topical, sublingual, mucosal, nasal, opthalmic, subcutaneous, intramuscular, intravenous, transdermal, spinal, intrathecal, intra-articular, intra-arterial, sub-arachniod, bronchial, lymphatic, and intrauterine administration. Alternatively, the invention may be used in ex vivo gene therapy, which involves the removal of cells, such as pluripotent stem cells, from an animal by various means known in the art, the ex vivo transfection of those cells with exogenous genetic materials, and the replacement of the resulting transformed cells into the same or another animal.

The present invention contemplates the use of pharmaceutical compositions or formulations for human medical use which comprise the cochleate vector structures of the present invention as therapeutic ingredients. Such pharmaceutical compositions may include pharmaceutically effective carriers, and optionally, may include other therapeutic ingredients. The carrier or carriers must be pharmaceutically acceptable in the sense that they are compatible with the therapeutic ingredients and are not unduly deleterious to the recipient thereof. The therapeutic ingredient or ingredients are provided in an amount necessary to achieve the desired therapeutic effect, described below.

The mode of administration and dosage forms will of course affect the therapeutic amounts of the compounds which are desirable and efficacious for the given treatment application. The genetic materials are delivered in an amount capable of causing the recipient to produce therapeutic molecules in a therapeutically effective amount. A therapeutically effective amount is an amount necessary to prevent, delay or reduce the severity of the onset of disease, or an amount necessary to arrest or reduce the severity of an ongoing disease. It will be readily apparent to one of ordinary skill in the art that this amount will vary based on factors such as the weight and health of the recipient, the type of cells being transformed, the mode of administration of the present compositions and the type of medical disorder being treated.

Formulations of the present invention can be presented as discrete units such as capsules, cachets, tablets or lozenges, each containing a predetermined amount of the vector delivery structure; or as a suspension.

As the following examples illustrate, DNA expression vectors containing AAV ITRs, when formulated with the AAV proteins Rep 68 and Rep 78 and a cochleate precipitate, can mediate successful gene transfer to human cells. The co-packaging of AAV Rep proteins and AAV ITR-containing DNA gene transfer vectors allows rapid gene transfer to resting cell targets following limited ex vivo manipulation in the absence of cytokine stimulation, resulting in long term gene transfer to pluripotent stem cells to potentially pluripotent stemcells.

As described in the examples below, adult or neonatal human $CD34^+$ progenitor cells can be transfected with marker genes by this method following brief ex vivo exposure to cochleate vector delivery structures in the absence of cytokine stimulation. Both the AAV ITR and the Rep proteins contribute to the efficiency of this process. This process is roughly five-fold more efficient than gene transfer by a standard retroviral vector in the absence of cytokine stimulation. Although standard retroviral gene transfer protocols employing cytokine stimulation result in more efficient gene transfer following three days of in vitro stimulation (see Experiment 3), the targets thus transfected have decreased capacity for hematopoietic reconstitution. In contrast, the methods of the present invention are superior to standard retroviral gene transfer as they allow rapid hematopoietic stem cell transduction in the absence of cytokine stimulation with probable maintenance of pluripotency.

EXAMPLES

The following examples demonstrate the efficacy of specific DNA protein cochleate complexes to achieve stable gene transfer and expression in human hematopoietic stem cells. Cochleates containing a plasmid encoding the iterated terminal repeat (ITR) sequence within the AAV genome and the Rep 68 and Rep 78 proteins, have been shown to have a higher efficiency of transduction than cochleates containing a plasmid with only one protein, or a plasmid which contains LTRs instead of ITRs.

The efficiency of transduction of a selectable marker gene (Neomycin resistance) can be assessed by the number of G418 resistant colonies produced. Stable gene transduction and expression of the neomycin phosphotransferase (neo) gene allows cellular replication and the growth of colonies in the presence of the antibiotic G418. Cells which are not stably transduced and expressing the protein, cannot survive in the presence of appropriate concentrations of G418.

The Rep 68 and Rep 78 proteins were expressed as maltose binding protein (MBP) fusion proteins in *E. coli* as described in Chiorini et al., "Biologically active proteins of adeno-associated virus type II produced as fusion proteins in *Escherichia coli*," Journal of Virology 68:797–804 (1994) (the disclosure of which is incorporated herein by reference). The bacterially-expressed proteins were purified over an amylose affinity column.

Figure 1:
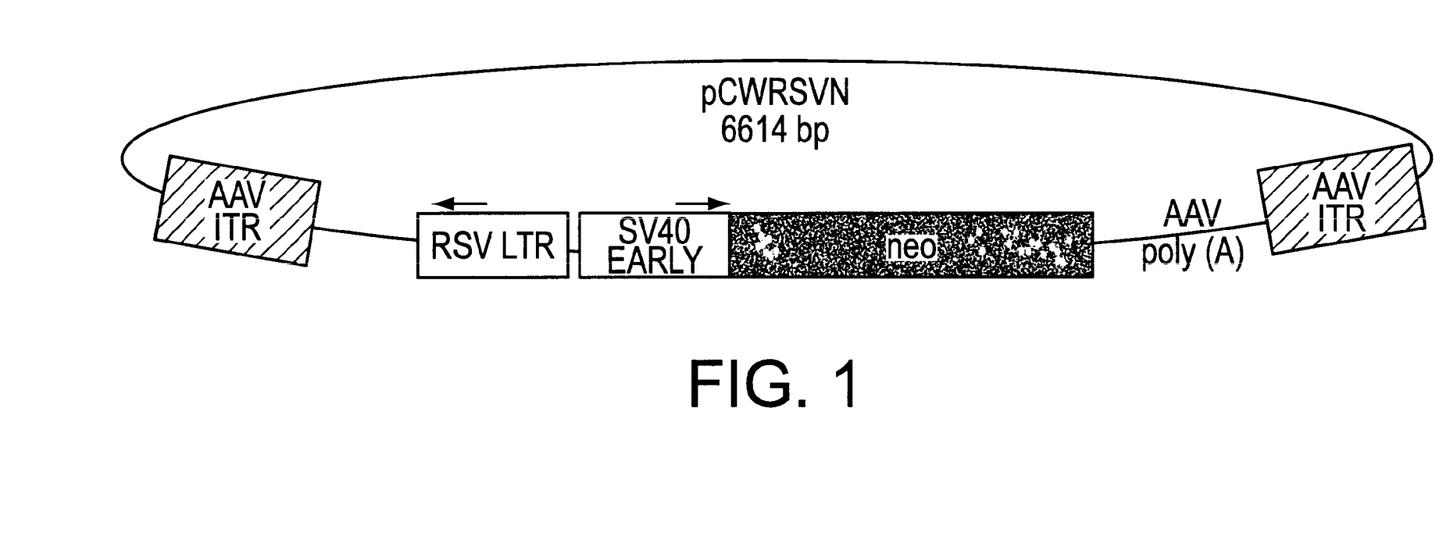
FIG. 1 is a diagram of a DNA plasmid gene vector (CWRSVN) containing an SV40-driven neomycin phosphotransferase (NEO) marker gene flanked by the 5' and 3' AAV ITRs.
Figure 2:
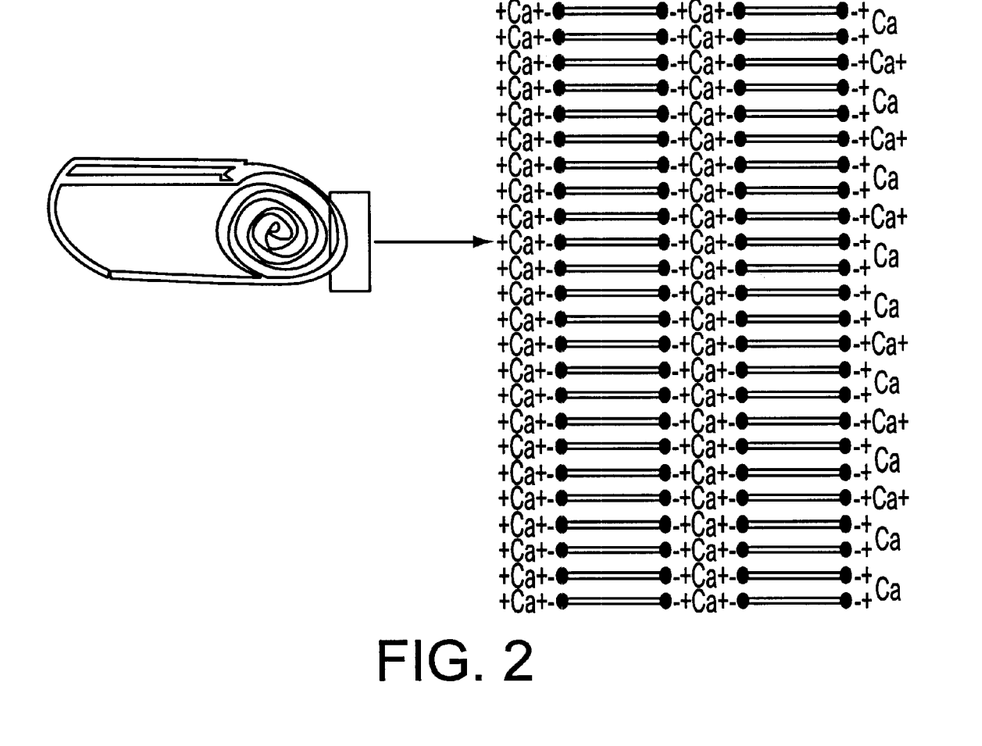
FIG. 2 is a diagrammatic representation of one conformation of a cochleate.
Figure 3A:
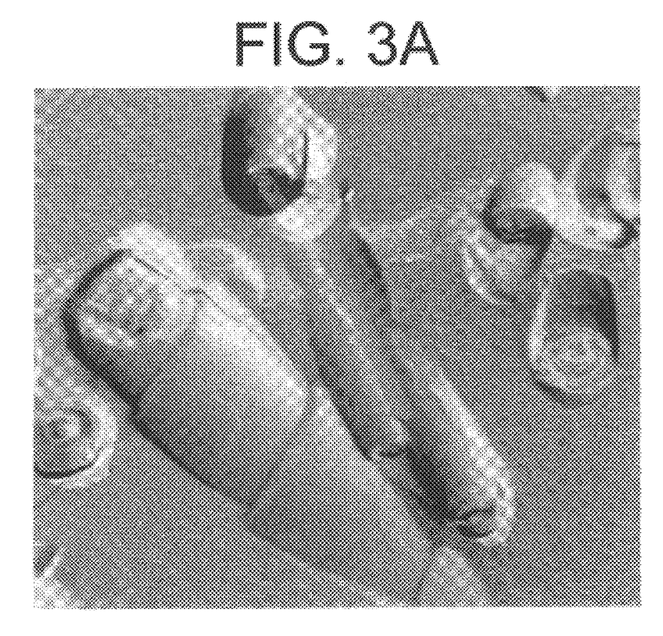
FIG. 3 is an illustration of freeze fractured cochleate precipitates as seen by transmission electron microscopy.
Figure 3B:
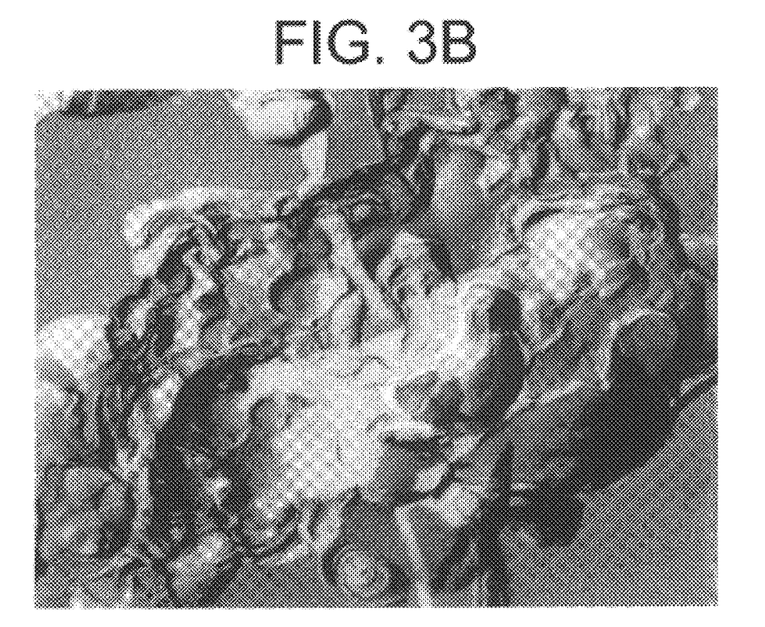

DNA plasmid gene transfer vector (CWRSVN) containing an SV40-driven neomycin phosphotransferase (neo) marker gene flanked by the 5' and 3' AAV ITRs (see FIG. 1) (Chatterjee et. al., "Dual target inhibition of HIV-1 in vitro by means of an adeno-associated virus antisense vector," Science 258:1485–1488 (1992), the disclosure of which is incorporated herein by reference)), was incorporated into cochleates (encochleated) by itself or co-packaged with either one or both of the Rep 68 and Rep 78 proteins.

The AAV rep proteins 68 and 78 bind specifically to the AAV ITRs, but do not bind to long terminal repeat sequences (LTRs) from murine leukemia virus (MMLV). As a control for the specificity of the rep protein-DNA interaction, the DNA vector G1EN, containing, an SV40-driven neomycin phosphotransferase (neo) marker gene flanked by the 5' and 3' MMLV LTRs (Morgan et al., "Retroviral vectors containing putative internal ribosome entry sited: development of a polycistronic gene transfer system and applications to human gene therapy." Nucleic Acids Research 20:1293–1299 (1992) (the disclosure of which is incorporated herein by reference)), was incorporated into cochleates by itself, or co-packaged with both of the Rep 68 and Rep 78 proteins.

Example 1

Formulation Protocol for Integrative DNA Vectors in Layered Lipid Bilayer Structures.

In initial studies, Rep proteins in buffer were incubated with plasmids to promote DNA protein complex formation. Plasmids (with or without proteins) were added gradually to dryed down lipids (phosphatidylserine (PS) and cholesterol (CHOL)), then voitexed. Calcium was added in small aliquots, with mixing, to form cochleates. Complexes were incubated at 37° C., then stored at 4° C.

General protocol for the formulation of integrative lipid DNA vectors utilized in the gene transfer experiments.

1. Add plasmids to appropriate tubes.
2. Add Rep proteins to appropriate tubes containing DNA.
3. Incubate at room temperature for one hour.
4. Dry down lipid in separate tubes.
5. Add buffer to lipids (e.g. enough to make DNA 0.33 mg/ml when added).
6. Vortex to resuspend lipids.
7. Sonicate to reduce size of liposomes.
8. Add buffers containing DNA and proteins to the lipids.
9. Blow nitrogen into tubes to replace air.
10. Vortex briefly.
11. Add soluble calcium with gentle shaking to mix.
12. Store 4° C.

Vector formulation can be varied by changing the ratio of DNA binding proteins to DNA. The current formulation consists of 0.66 to 1.0 ratio by weight; 33 to 1.0 ratio by mole. A probable range of useful ratios for formulation would be from 1:1 to 1000:1 molar ratio of DNA binding protein to sequences in DNA to which they bind.

Macroscopically, the final formulations consisted of heavy white suspensions. Phase contrast, light microspic observation (1000×) indicated heavy suspensions of refractile granular crystals, free and in aggregates. Cochleate structure of the crystals was confirmed by addition of EDTA, which caused conversion of the cochleate crystals to liposomes.

Example 2

Specific Formulations Utilized in the Gene Transfer Experiments.

Conditions to promote formation of DNA-binding protein complexes may vary but can be determined experimentally. Conditions used were TES buffer (100 mM NaCl, 2 Mm TES, 2 mM histidine, pH 7.4) at approximately 2 times the volume of protein in the buffer it was purified in (HEPES buffered, pH 7.5, 150 mM KCl, 1 mM MgCl$_2$, 0.1 mM EDTA, and 10 mM maltose) using a ratio of DNA to lipid of 1.0: 10.0 by weight. A probable range of useful ratios for formulations would be from 1:1 to 1:100 by weight.

Cochleates were formulated using:

1. no DNA vector or Rep proteins;
2. The DNA vector G1EN, and no Rep proteins;
   G1EN and Rep 68 and Rep 78 proteins;
4. CWRSVN and no Rep proteins;
5. CWRSVN and Rep 68 protein;
6. CWRSVN and Rep 78 protein; and
7. CWRSVN and Rep 68 and 78.

TABLE 1

Formulation compositions of examples described above.
(DNA to lipid ratio, 1:10 by weight, and protein to DNA ratio 0.66:1 by wt.)

| | Formulation number | | | | | | |
|---|---|---|---|---|---|---|---|
| Component | 1 | 2 | 3 | 4 | 5 | 6 | 7 |
| Buffer | 1.5 ml | 1.1 ml | 1.1 ml | 1.35 ml | 1.35 ml | 1.35 ml | 1.35 ml |
| G1EN | 0 | 0.5 mg | 0.5 mg | 0 | 0 | 0 | 0 |
| CWRSVN | 0 | 0 | 0 | 0.5 mg | 0.5 mg | 0.5 mg | 0.5 mg |
| Rep 68 | 0 | 0 | 0.33 mg | 0 | 0.33 mg | 0 | 0.33 mg |

TABLE 1-continued

Formulation compositions of examples described above.
(DNA to lipid ratio, 1:10 by weight, and protein to DNA ratio 0.66:1 by wt.)

| Component | Formulation number | | | | | | |
|---|---|---|---|---|---|---|---|
| | 1 | 2 | 3 | 4 | 5 | 6 | 7 |
| Rep 78 | 0 | 0 | 0.33 mg | 0 | 0 | 0.33 mg | 0.33 mg |
| PS | 4.5 mg | 4.5 mg | 4.5 mg | 4.5 mg | 4.5 mg | 4.5 mg | 4.5 mg |
| CHOL | 0.5 mg | 0.5 mg | 0.5 mg | 0.5 mg | 0.5 mg | 0.5 mg | 0.5 mg |
| 0.1 M $CaCl_2$ | 120 µl | 120 µl | 120 µl | 120 µl | 120µl | 120 µl | 120 µl |

Example 3

Gene Transfer Experiments Using Integrative Lipid DNA Vectors.

Human $CD34^+$ progenitor cell targets were obtained from neonatal cord blood or by cytopheresis of granulocyte-macrophage colony-stimulating factor (GM-CSF) pre-treated adult volunteers under a University of Maryland, Baltimore-approved human use protocol.

Peripheral blood mononuclear cells were then further enriched for $CD34^+$ targets by positive selection using a CellPro (Bothell, Wash.) immuno-affinity column.

In a typical transduction (in vitro gene transfer experiment), 40,000 cord blood or adult $CD34^+$ cell targets were re-suspended in 200 µl RPMV 10% FCS and incubated with a 5 µl vector-cochleate suspension (1.33% of the total culture volume) containing 1.66 µg DNA, 16.6 µg lipid and 2.2 µg protein cochleates at 37° C. for 12 hours. Cells were then immediately plated in Methocult HC (Stem Cell Tech., Vancouver) with G418 to measure the ability of stem cells to express the transferred marker gene neo and form colonies. A probable range of useful transduction conditions would include 40,000 cell targets in 200 µl of medium incubated in the presence of a vector-cochleate suspension consisting of from 0.1 µg DNA, 1.0 µg lipid, 0.13 µg protein to 10 µg DNA, 100 µg lipid, 13 µg protein. The number of cells can be varied as can the volume of cochleate suspension.

Initial toxicity studies were performed with no G418 selection to determine the range of concentrations of cochleates to be used. For 40,000 cells in 200 µl of medium, 25 µl vector suspension (6.64 µg DNA, 66.4 µg lipid, 11.0 µg protein) and higher showed some toxicity, whereas 15 µl vector suspension (5 µg DNA, 50 µg lipid, 6.6 µg protein) and lower showed minimal or no toxicity. Results of gene transfer experiments utilizing the above described formulations are shown below.

Gene transfer experiment 1
Neonatal blood cord $CD34^+$ cells in 1 mg/ml G418

| Cochleate Type | Colonies/30 fields* |
|---|---|
| No Cochleates | 20 |
| CWRSVN Cochleates alone | 23 |
| CWRSVN Cochleates/Rep 68 | 26 |
| CWRSVN Cochleates/Rep 78 | 27 |
| CWRSVN Cochleates/Rep 68 and Rep 78 | 38 |

*mean of duplicate plates

Gene transfer experiment 2
Neonatal cord blood $CD34^+$ cells in 1.5 mg/ml G418

| Cochleate Type | Colonies/30 Fields* | |
|---|---|---|
| | Range | Mean |
| No cochleates | N/A | 0 |
| No cochleate/no G418 | N/A | 148 |
| G1EN cochleate/Rep 68 & 78 | 0–6 | 3.67 (sd 2.62) |
| CWRSVN cochleate alone | 2–4 | 3.0 (sd 0.81) |
| CWRSVN cochleate/Rep 68 & 78 | 9–12 | 10.67 (sd 1.24) |

*counted in triplicate plates

Gene transfer experiment 3
Neonatal cord blood CD34+ cells in 1.5 mg/ml G418

| Cochleate Type | Colonies/30 Fields* | |
|---|---|---|
| | Range | Mean |
| No cochleate | 0 | 0 |
| No cochleates/no G418 | 60–65 | 62 |
| G1EN cochleate/Rep 68 & 78 | 0 | 0 |
| CWRSVN cochleate alone | 0–3 | 1.5 (sd 1.1) |
| G1EN retroviral vector** | 1–2 | 1.4 (sd 0.2) |
| G1EN retroviral vector*** | 16–26 | 18.3 (sd 5.4) |
| CWRSVN cochleate/Rep 68 & 78 | 2–8 | 5.25 (sd 2.2) |

*counted in quadruplicate plates
**standard MMLV retroviral vector expressing neo resistance
***transduced with cytokines for 3 days (standard retroviral transduction procedure)

Gene transfer experiment 4
Adult CD34+ cells in 2 mg/ml G418

| Cochleate Type | Colonies/30 Fields* | |
|---|---|---|
| | Range | Mean |
| No cochleate | 0 | 0 |
| CWRSVN cochleates alone | 0–6 | 1.7 |
| CWRSVN cochleates/Rep 68 | 0–10 | 3.6 |
| CWRSVN cochleates/Rep 68 & 78 | 6–12 | 9.7 |
| G1EN cochleates/Rep 68 & 78 | 0 | 0 |
| G1EN retroviral vector** | 0 | 0 |

*counted in triplicate plates
**standard MMLV retroviral vector expressing neo resistance Conclusions from Gene Transfer Experiments.

These results demonstrate that a gene vector flanked by the AAV ITRs and formulated with Rep 68 and Rep 78 proteins and cochleates can transfer a marker gene capable of being expressed over 10 to 14 days in culture in hematopoietic colony-forming, cells. Both the AAV ITR and the Rep proteins contribute to the efficiency of this process. This process is roughly five-fold more efficient than gene transfer by a standard retroviral vector in the absence of cytokine stimulation. Although standard retroviral gene transfer protocols employing cytokine stimulation result in more efficient gene transfer following three days of in vitro stimulation (see Experiment 3), the targets transduced have decreased long term repopulating capacity.

Example 4
Treatment of Genetically Abnormal Hematopoietic Progenitor Cells with Therapeutic Genes Using Integrative Lipid DNA Vectors.

A therapeutic gene vector flanked by the AAV ITR's and co-packaged with Rep 68 and Rep 78 proteins in a cochleate can be used for transfection and treatment of genetically abnormal hematopoietic progenitor cells including stem cells. Examples of therapeutic genes and the hematopoietic disorder that they are associated with include a normal beta globin gene to be expressed in red blood cells to correct for beta thalassemia or sickle cell anemia, a normal gene for adenosine deaminase to be expressed in lymphocytes to correct some forms of severe combined immune deficiency, normal p47 or p67 phox (phagocytic oxidase) gene in phagocytic cells to correct chronic granulomatous disease, and a gene encoding antisense RNA against a transforming oncogene contributing to leukemia or lymphoma such as anti-myc for Burkitt's lymphoma.

Example 5
Circulating Natural or Synthetic Biologically Active Factors for Replacement, Correction or Modulation of Metabolic Pathways.

A therapeutic gene vector flanked by the AAV ITR's and co-packaged with Rep 68 and Rep 78 proteins in a cochleate can be used for transient or stable transfection in order to replace, correct or modulate functions in metabolic pathways. This can be accomplished through the transfection of a variety of cell types depending on the application such as lung, skin and liver. Examples of therapeutic genes and the blood disorder that they are associated with include a normal gene for C1 (complement protein) inhibitor for treatment of hereditary angioneurotic oedema, a normal gene for a clotting factor for treatment of hemophilia, and a normal gene for insulin for treatment of diabetes.

Example 6
Treatment of Cancer Cells with Therapeutic Genes Using Integrative Lipid DNA Vectors.

A therapeutic gene vector flanked by the AAV ITR's and co-packaged with Rep 68 and Rep 78 proteins in a cochleate can be used for transfection and treatment of cancer cells. Examples of therapeutic genes and the effect that the expressed gene would have include a normal regulatory gene to restore controlled growth, such as p53 and retinoblastoma, and a normal gene for a protein or RNA that regulates the expression of other altered or overexpressed genes which are responsible for oncogene or metastatic behavior, such as ras, myc, fas ligand, and surface receptors.

Example 7
Formulation Protocol for Prokaryotic and Eukaryotic Integrative Protein/DNA Vectors in Layered Lipid Bilayer Structures.

General protocol for the formulation of prokaryotic and eukaryotic integrative lipid DNA vectors.

1. Add plasmids to appropriate tubes.
2. Add integrative proteins to appropriate tubes containing DNA.
3. Incubate at room temperature for one hour.
4. Dry down lipid in separate tubes.
5. Add buffer to lipids (e.g. enough to make DNA 0.33 mg/ml when added).
6. Vortex to resuspend lipids.
7. Sonicate to reduce size of liposomes.
8. Add buffers containing DNA and proteins to the lipids.
9. Blow nitrogen into tubes to replace air.
10. Vortex briefly.
11. Add soluble calcium with gentle shaking to mix.
12. Store 4° C.

Vector formulation can be varied by changing the ratio of DNA binding proteins to DNA. Other integrative protein/DNA structures that can be used are transposable elements from prokaryotic and eukaryotic organisms which include bacteria, yeast, viruses, animal cells, and plant cells. Examples of transposable elements include retrotransposases and their DNA sequence substrates from retrotransposons from yeast, bacterial or bacteriophage transposase proteins and their substrate sequences, and retroviral integrases and the long terminal repeat (LTR) sequences to which they bind and catalyze integration into host cell chromosomes (e.g., Rous sarcoma or HIV-1 or -2).

What is claimed is:
1. A vector delivery stricture comprising:
   a) a cochleate comprising a lipid bilayer element and cations;
   b) one or more proteins that facilitate the integration of one or more nucleotide sequences, that can express a molecule, into the genome of a host cell; and
   c) a polynucleotide comprising one or more DNA sequences recognized and bound by the one or more proteins and one or more oligonucleotides or polynucleotides, each containing said one or more nucleotide sequences.
2. The vector delivery structure of claim 1, wherein the polynucleotide is selected from the group consisting of a plasmid or nucleic acid construct.
3. The vector delivery structure of claim 1, wherein the structure further included a polynucleotide that expresses one or more proteins that facilitate integration.
4. The vector delivery structure of claim 1, wherein the cations are divalent cations.
5. The vector delivery structure of claim 1, wherein the cations are calcium.
6. The vector delivery structure of claim 1, wherein the one or more proteins that facilitate the integration of one or more nucleotide sequences into the genome of a host cell are one or more binding proteins that have a DNA binding motif.
7. The vector delivery structure of claim 6, wherein the one or more binding proteins are from adeno-associated virus type II.
8. The vector delivery structure of claim 6, wherein the one or more binding proteins are at least one adeno-associated virus protein selected from the group consisting of Rep 68 and Rep 78.
9. The vector delivery structure of claim 6, wherein the one or more binding proteins comprise Rep 68 and Rep 78.
10. The vector delivery structure of claim 1, 8 or 9, wherein the one or more DNA sequences recognized and bound by the one or more proteins are the inverted terminal repeat regions of adeno-associated virus.

11. The vector delivery structure of claim 10, wherein the one or more oligonucleotides or polynucleotides comprise a length of DNA that is flanked at each end by at least one of the inverted terminal repeat regions.

12. The vector delivery structure of claim 6, wherein at least one of the one or more binding proteins is an integrase and at least one of the one or more DNA sequences recognized and bound by the one or more binding proteins is a substrate for said integrase.

13. The vector delivery structure of claim 12, wherein at least one of the one or more binding proteins is an integrase that is not Rep 68 or Rep 78.

14. The vector delivery structure of claim 6, wherein at least one of the one or more binding proteins is a helicase and at least one of the one or more DNA sequences recognized and bound by the one or more binding proteins is a substrate for said helicase.

15. The vector delivery structure of claim 6, wherein at least one of the one or more binding proteins is a DNA excision enzyme and at least one of the one or more DNA sequences recognized and bound by the one or more binding proteins is a substrate for said DNA excision enzyme.

16. The vector delivery structure of claim 6, wherein at least one of the one or more binding proteins is an isomerase and at least one of the one or more DNA sequences recognized and bound by the one or more binding proteins is a substrate for said isomerase.

17. The vector delivery structure of claim 6, wherein at least one of the one or more binding proteins is a telomerase and at least one of the one or more DNA sequences recognized and bound by the one or more binding proteins is a substrate for said telomerase.

18. The vector delivery structure of claim 6, wherein at least one of the one or more binding proteins is a DNA repair enzyme and at least one of the one or more DNA sequences recognized and bound by the one or more binding proteins is a substrate for said DNA repair enzyme.

19. The vector delivery structure of claim 1, wherein at least one of the one or more proteins that facilitate the integration of the one or more nucleotide sequences into the genome of the host cell is a protein that has gene regulatory activity and at least one of the one or more DNA sequences recognized and bound by the one or more binding proteins is a substrate for said protein that has gene regulatory activity.

20. The vector delivery structure of claim 1, wherein at least one of the one or more proteins that facilitate the integration of the one or more nucleotide sequences into the genome of the host cell is a protein that facilitates transport to or uptake by the nucleus of the host cell.

21. The vector delivery structure of claim 1, wherein the host cell is a human cell.

22. The vector delivery structure of claim 1, wherein the host cell is a pluripotent stem cell.

23. A vector delivery structure for delivering to the interior of a host cell one or more nucleotide sequences, that can express a molecule, and one or more proteins that bind to DNA for the integration of the one or more nucleotide sequences into the genome of the host cell, the vector delivery structure comprising:

a) a cochleate comprising a lipid bilayer element wherein the layers of the lipid bilayer element are bound together by a divalent calcium cation;

b) a DNA binding protein of adeno-associated virus type II comprising a Rep 68 protein or a Rep 78 protein; and c) a polynucleotide comprising one or more inverted terminal repeat regions of adeno-associated virus type II and one or more oligonucleotides or polynucleotides, each containing said one or more nucleotide sequences.

24. The vector delivery structure of claim 23, wherein the polynucleotide is selected from the group consisting of a plasmid or nucleic acid construct.

25. The vector delivery structure of claim 23, wherein, the one or more oligonucleotides or polynucleotides comprise a length of DNA that is flanked at each end by at least one inverted terminal repeat regions.

26. The vector delivery structure of claim 23, 24 or 25, wherein the structure does not include a polynucleotide that expresses one or more proteins that facilitate integration.

27. The vector delivery structure of claim 23, wherein the host cell is a human cell.

28. The vector delivery structure of claim 23, wherein the host cell is a pluripotent stem cell.

* * * * *